United States Patent [19]

Yamaguchi et al.

[11] Patent Number: 5,139,626

[45] Date of Patent: Aug. 18, 1992

[54] ION CONCENTRATION MEASUREMENT METHOD

[75] Inventors: Shuichiro Yamaguchi, Fuji; Takeshi Shimomura; Norihiko Ushizawa, both of Fujinomiya, all of Japan

[73] Assignee: Terumo Corporation, Tokyo, Japan

[21] Appl. No.: 607,856

[22] Filed: Oct. 31, 1990

Related U.S. Application Data

[63] Continuation of Ser. No. 412,566, Sep. 25, 1989, abandoned, which is a continuation of Ser. No. 198,593, May 20, 1988, abandoned, which is a continuation of Ser. No. 913,458, Sep. 30, 1986, abandoned.

[30] Foreign Application Priority Data

Oct. 2, 1985 [JP] Japan ............................ 60-219882

[51] Int. Cl.$^5$ ............................................ G01N 27/333
[52] U.S. Cl. ........................... 204/153.1; 204/153.13; 204/153.15; 204/153.16; 204/153.21; 204/294; 204/416; 204/418
[58] Field of Search ............... 204/153.1, 416–419, 204/435, 153.13, 153.15, 153.16, 153.21

[56] References Cited

U.S. PATENT DOCUMENTS

| | | | |
|---|---|---|---|
| 3,598,713 | 8/1971 | Baum et al. | 204/417 |
| 3,926,764 | 12/1975 | Ruzicka et al. | 204/418 |
| 3,932,233 | 1/1976 | Ruzicka | 204/418 |
| 3,957,612 | 5/1976 | Niedrach | 204/415 |
| 3,957,613 | 5/1976 | Macur | 204/415 |
| 4,052,285 | 10/1977 | Dobson | 204/418 |
| 4,115,209 | 9/1978 | Fraiser et al. | 204/418 |
| 4,198,851 | 4/1980 | Janata | 73/23 |
| 4,214,968 | 7/1980 | Battaglia et al. | 204/435 |
| 4,280,889 | 7/1981 | Szonntagh | 204/420 |
| 4,305,802 | 12/1981 | Koshishi | 204/419 |
| 4,440,603 | 4/1984 | van Effen et al. | 204/400 |
| 4,454,007 | 6/1984 | Pace | 204/1 T |
| 4,512,870 | 4/1985 | Kohara et al. | 204/416 |
| 4,549,951 | 10/1985 | Knudson et al. | 204/416 |
| 4,561,962 | 12/1985 | Kankare | 204/415 |
| 4,563,263 | 1/1986 | Oyama et al. | 204/418 |
| 4,579,641 | 4/1986 | Shimomura et al. | 204/403 |
| 4,582,589 | 4/1986 | Ushizawa et al. | 204/418 |
| 4,615,954 | 10/1986 | Solomon et al. | 429/27 |
| 4,632,732 | 12/1986 | Fog et al. | 204/1 T |
| 4,647,363 | 3/1987 | Holscher | 204/415 |
| 4,753,715 | 6/1988 | Yamaguchi et al. | 204/418 |
| 4,798,664 | 1/1989 | Yamaguchi et al. | 204/418 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/414 |
| 5,282,079 | 8/1981 | Chang et al. | 204/420 |

FOREIGN PATENT DOCUMENTS

| | | |
|---|---|---|
| 56283 | of 0000 | European Pat. Off. |
| 01186210 | 7/1986 | European Pat. Off. |
| 3134760A | 9/1982 | Fed. Rep. of Germany |
| 35-52759 | 3/1960 | Japan |
| 52-30490 | 8/1977 | Japan |
| 57-6344 | 4/1982 | Japan |
| 57-196116 | 12/1982 | Japan |
| 58167951 | of 1983 | Japan |
| 59-57156 | 4/1984 | Japan |
| 59-164952 | 9/1984 | Japan |
| 60-7357 | 1/1985 | Japan |
| 60-73351 | 4/1985 | Japan |
| 60-128345 | 7/1985 | Japan |

OTHER PUBLICATIONS

Nanjo et al, *Anal. Chim. Acta*, vol. 75 (1975), pp. 169–180.

(List continued on next page.)

*Primary Examiner*—T. Tung
*Attorney, Agent, or Firm*—Burns, Doane, Swecker & Mathis

[57] ABSTRACT

An electrochemical cell is formed by immersing an electrochemical ion sensor and a reference electrode into a solution of interest, the electrochemical ion sensor exhibiting ion selectivity with respect to an ion of interest and having a high electrode resistance. A current which flows through the electrochemical cell is measured while the potential of the electrochemical ion sensor is held to a constant potential with respect to the reference electrode. The current so obtained are proportional to the logarithm value of the concentration of the ion.

3 Claims, 6 Drawing Sheets

OTHER PUBLICATIONS

Guilbault et al, *Anal. Chim. Acta., vol. 69 (1974), pp. 183-188.*

Ma et al, "Organic Analysis Using Ion Selective Electrodes", vol. 2, (1982), pp. 60 and 62.

Ryan, "Electrochemical Detectors", (1984), p. 7.

Ammaun, "Ion-Selective Microelectrodes", Principles, Design & Application, pp. 5-7, 66, 100.

Tamura et al, "Coated Wire Sodium- and Potassium-Electrodes Based on Bis(crown ether) Compounds", Analytical Chemistry, vol. 54, No. 7, Jun. 1982, pp. 1224-1227.

Wuthier et al, "Tin Organic Compounds as Neutral Carriers for Anion Selective Electrodes", Analytical Chemistry, vol. 56, No. 3, Mar. 1984, pp. 535-538.

Norov et al, "Calcium-Selective Electrode Without an Internal Reference Solution", Journal of Analytical Chemistry, vol. 43, No. 8, Part 1, Aug. 1979, pp. 1159-1162.

Oyama et al, "Hydrogen Ion Selective Microelectrode Prepared by Modifying An Electrode With Polymers", Analytical Chemistry 1987, vol. 59, pp. 258-262, Jan. 1987.

Oyama, "Ion Selective Microelectrode Prepared By Modifying An Electrode With Polymers", International electrical Symposium, Schaumberg, Ill., May 27-29 (1987), pp. 122-125.

Oyama et al, "A New Type of Ion-Selective Microelectrodes Using Electropolymerize Thin Films", j-4 Bioelectroanalytical Chemistry Symposium, Honolulu, Hi., Oct. 18-23, 1987.

Oyama et al "Electrochemical Properties of Electropolymerized Poly (1-pyrenamine) Films", The Chemical Society of Japan, Jul. 1986.

Oyama et al, "Ion Selective Electrode Prepared By Modifying an Electrode With Polymers", Tokyo Seminar on Macromolecular Complexes, Tokyo Univ., Oct. 14-17, 1987.

ION CONCENTRATION MEASUREMENT METHOD

This application is a continuation of application Ser. No. 412,566, filed Sep. 25, 1989, now abandoned, which is a continuation of application Ser. No. 198,593, filed May 20, 1988, now abandoned, which is a continuation of application Ser. No. 913,458, filed Sep. 30, 1986, now abandoned.

BACKGROUND OF THE INVENTION

1. Field of the Invention

This invention relates to a novel method of measuring ionic concentration More particularly, the invention relates to a method of measuring ionic concentration amperometrically using an electrochemical ion sensor.

2. Description of the Prior Art

In general, the measurement of ionic concentration in the prior art entails utilizing a potentiometric method, according to which ionic concentration is determined by measuring equilibrium potential. Since equilibrium potential varies with the logarithm of ionic concentration, an advantageous feature of the potentiometric method is that even low concentrations can be measured with good precision.

With an amperometric method, on the other hand, observed current values and ionic concentration are proportionally related, as a result of which precise measurement of low concentrations involves great difficulty. For this reason, measurement of ionic concentration by amperometry has not come into practical use.

SUMMARY OF THE INVENTION

In view of these circumstances, the inventor has conducted a variety of researches and has perfected the present invention upon discovering that it is possible to measure ionic concentration amperometrically if use is made of an electrode of a certain type.

The present invention provides an ionic concentration measurement method characterized by forming an electrochemical cell by immersing an electrochemical ion sensor and a reference electrode into a solution of interest, said electrochemical ion sensor exhibiting ion selectivity with respect to an ion of interest and having a relative high electrode resistance, and measuring a current which flows through said cell while the electrochemical ion sensor is held at a constant potential with respect to the reference electrode.

Further, according to the ionic concentration method of the present invention, the electrochemical ion sensor comprises an electrically conductive substrate, a redox layer deposited on a surface of said electrically conductive substrate and an ion selective layer, which exhibits ion selectivity with respect to an ion of interest, deposited on a surface of said redox layer.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 2:
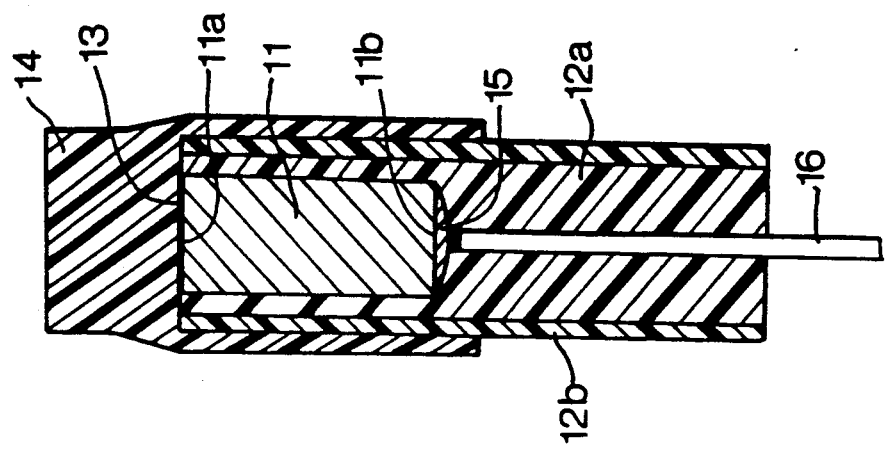
FIG. 2 is an enlarged sectional view useful in describing a pH sensor.

An electrochemical ion sensor employed in the present invention must exhibit ion selectivity to the ion of interest and must have a high electrode film resistance. Since the inventive method relies upon amperometry, using an electrochemical ion sensor that is not ion-selective to the ion of interest is undesirable because measurement errors will be produced by the influence of ions of a type other than the ion of interest, and by the influence of an electrolytic current of these substances reacting with the electrode. Using an electrode film resistance that is not sufficiently high is undesirable since the current flowing through the battery will grow large in magnitude and greatly increase the amount of the ion of interest electrolyzed, thus making it impossible to measure the equilibrium concentration of the ion of interest. Accordingly, it is required that the electrochemical ion sensor used in the present invention be such that the current flowing in the electrode interface is controlled essentially by the film resistance. In view of the foregoing, an electrochemical ion sensor suitable for use in the present invention ordinarily has a coefficient of selection of not more than $10^{-1}$ with respect to ions other than the ion of interest and an electrode film resistance of not less than $10^3 \Omega/cm^2$.

An example of an electrochemical ion sensor that satisfies the above conditions is one comprising an electrically conductive substrate, a film having a reversible redox function deposited on the surface of the electrically conductive substrate, and an ion selective film deposited on the surface of the first-mentioned film. More specifically, the electrically conductive substrate used in the ion sensor may consist of an electrically conductive carbon material such as basal plane pyrolytic graphite (hereafter referred to as "BPG") or glassy carbon, a metal such as gold, platinum, copper, silver, palladium, nickel or iron, especially a precious metal, or a composite obtained by coating any of these metals with a semiconductor such as indium oxide or tin oxide. The electrically conductive carbon material is preferred, especially BPG.

The redox layer refers to one in which an electrode comprising an electrically conductive substrate having this layer deposited on its surface is capable of generating a constant potential on the substrate owing to a redox reaction. In the present invention, an especially preferred redox layer is one which will not allow the potential to fluctuate due to the partial pressure of oxygen gas. Particularly suitable examples of the redox layer are (1) an organic compound membrane or a polymeric membrane capable of a quinone-hydroquinone type redox reaction, and (2) an organic compound membrane or polymeric membrane capable of an amine-quinoid type redox reaction, and (3) electrically conductive material (e.g. polypyrrole and poly thionylone). The quinone-hydroquinone type redox reaction is expressed by e.g. the following reaction formula, taking a polymer as an example:

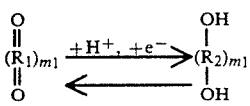

where $R_1$, $R_2$ represent e.g. compounds having a structure containing an aromatic series.

The amine-quinoid type redox reaction is expressed by e.g. the following reaction formula, taking a polymer as an example:

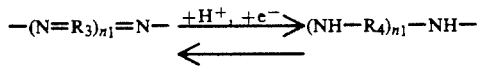

where $R_3$, $R_4$ represent e.g. compounds having a structure containing an aromatic series.

The following compounds (a)–(d) can be mentioned as compounds capable of forming the abovementioned layer having the redox function:

(a) A hydroxy aromatic compound expressed by

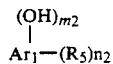

where $Ar_1$ represents an aromatic nucleus, $R_5$ a substituent group, $m_2$ is 1 or the effective valence of $Ar_1$, and $n_2$ is 0 or the effective valence of $Ar_1$ minus 1.

The aromatic nucleus of $Ar_1$ may be a single ring such as a benzene nucleus, a multiple ring such as an anthracene nucleus, pyrene nucleus, chrysene nucleus, perylene nucleus or coronene nucleus, or a heterocyclic ring. Examples of the substituent group $R_5$ are alkyl groups such as a methyl group, aryl groups such as a phenyl group, and a halogen atom. More specifically, examples are dimethyl phenol, phenol, hydroxy pyridine, o- and m-benzyl alcohols, o-, m- and p-hydroxybenzaldehydes, o- and m-hydroxyacetophenones, o-, m- and p-hydroxypro-piophenones, o-, m- and p-hydroxybenzophenones, o-, m- and p-carboxyphenols, diphenylphenol, 2-methyl-8-hydroxy-quinoline, 5-hydroxy-1, 4-napthoquinone, 4-(p-hydroxy-phenyl)2-butanone, 1, 5-dihydroxy-1, 2, 3, 4-tetra-hydronaphthalene, bisphenol-A, salicylanilide, 5- and 8-hydroxyquinolines, 1,8-dihydroxyanthraquinone, and 5-hydroxy-1,4-naphthoquinone.

(b) An amino aromatic compound expressed by the formula

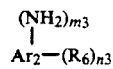

where $Ar_2$ represents an aromatic nucleus, $R_6$ a substituent group, $m_3$ is 1 or the effective valence of $Ar_2$, and $n_3$ is 0 or the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminophenantherene, 9-aminophenantherene, 9, 10-diaminophenantherene, 1-aminoanthraquinone, p-phenoxyaniline, o-phenylenediamine, p-chloroaniline, 3,5-dichloroaniline, 2,4,6-trichloroaniline, N-methylaniline, and N-phenyl-p-phenylenediamine.

(c) A quinone such as 1,6-pyrenequinone, 1,2,5,8-tetrahydroxynalizaline, phenantherenequinone, 1-aminoanthraquinone, purpurine, 1-amino-4-hydroxyanthraquinone, and anthralphyne.

Among these compounds, 2,6-xylenol and 1-aminopyrene are especially preferred.

(d) Pyrrole and derivatives thereof (e.g. N-methyl pyrrole), and thiophene and derivatives thereof (e.g. methyl thiophene).

Further, examples of compounds capable of forming the layer having the redox function are those which undergo a redox reaction The following can be mentioned: poly(N-methyl aniline) [Onuki, Matsuda, Oyama, Nihon Kagakukaishi, 1801–1809 (1984)], poly(2,6-dimethyl-1,4-phenylene ether), poly(o-phenylenediamine), poly(phenol) and polyxylenol; organic compounds containing the compounds (a) through (d) such as pyrazoronequinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds of (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the electrically conductive substrate, a polymer is obtained by synthesizing an amino aromatic compound, a hydroxy aromatic compound or the like on an electrically conductive substrate of electrically conductive carbon or a precious metal by an electrolytic oxidation polymerization method or electro-deposition method, or a polymer synthesized by application of electron beam irradiation, light or heat, is dissolved in a solvent The resulting solution is deposited on the electrically conductive substrate by painting or dipping. Among these three methods, the most preferred is electrolytic oxidation polymerization method. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the electrically conductive substrate. Preferred examples of the solvent are acetonitrile, water, dimethyl formamide, dimethyl sulfoxide, propylene carbonate and the like. Preferred examples of the supporting electrolyte are sodium perchlorate, sulfuric acid, sodium sulfate, phosphoric acid, boracic acid, tetrafluoro-potassium phosphate, quaternary ammonium salts and the like.

The deposited polymeric film generally exhibits a high density and is capable of blocking the permeation of oxygen, even if thin. To be usable in the present invention, the redox film should exhibit oxidation-reduction reactivity. Other than this, no particular limitation is placed upon the film, including the density thereof.

The membrane thickness of the redox layer is 0.01 um –0.5 mm, preferably 0.1–10 $\mu$m. A membrane thickness of less than 0.01 $\mu$m does not fully bring forth the effects of the invention, while a thickness of more than 0.5 mm is undesirable from the viewpoint of miniaturizing the sensor.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to coat the electrically conductive substrate with the redox layer and then immerse the resulting membrane into a solution of the electrolyte. As the ion-sensitive layer coating on the redox layer, use can be made of a membrane (a neutral carrier membrane) in which an ion carrier material selective to the ion of interest and, if necessary, an electrolytic salt, are carried on a polymeric compound The following are examples of the ion carrier material which can be used, depending upon the ion of interest:

(i) For hydrogen ion

Examples of a hydrogen ion carrier material, which were proposed before by Noboru Oyama (one of the inventors of the present invention), are amines expressed by the formula

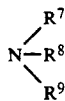

(where $R^7$, $R^8$, $R^9$ represent the same or different alkyl groups, among which at least two alkyl groups have a carbon number of 8-18), and compounds expressed by the formula

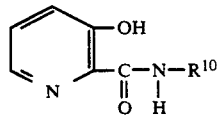

(where $R^{10}$ represents an alkyl group having a carbon number of 8-18). Tri-n-dodecylamine is especially preferred.

(ii) For potassium ion

Examples of which can be mentioned are valinomycin, nonactin, monactin, crown ether compounds such as dicyclohexyl-18-crown-6, naphtho-15-crown-5, bis(15-crown-5) and the like. Among these, valinomycin and bis(15-crown-5) are ideal.

(iii) For sodium ion

Examples which can be mentioned are aromatic amides or diamides, aliphatic amides or diamides, and crown compounds, e.g. bis[12-crown-4)methyl] dodecylmalonate, N,N,N,N-tetrapropyl-3,6-dioxanate diamide, N,N,N,N-tetra-benzyl-1,2-ethylenedioxy diacetoamide, N,N'-dibenzyl-N,N'-diphenyl-1,2-phenylendiacetoamide, N,N',N''-triheptyl-N,N'N''-trimethyl-4,4',4''-propylpyridine tris(3-oxythabutylamide), 3-methoxy-N,N,N,N-tetrapropyl-1,2-phenylendioxydiacetoamide, (-)-(R,R)-4,5-dimethyl-N,N,N,N-tetrapropyl-3,6-dioxaoctanediamide, 4-methyl-N,N,N,N-tetrapropyl-3-6-dioxaoctane diamide, N,N,N,N-tetrapropyl-1,2-phenylenedioxydiacetoamide, N,N,N,N-tetrapropyl-2,3-naphthanedioxydiacetoamide, 4-t-butyl-N,N,N,N-tetrapropyl-1,2-dichlorohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide. Among these, bis[(12-crown-4) methyl] dodecylmalonate is well-suited for use.

(iv) For chlorine ion

Examples which can be mentioned are quaternary ammonium salts expressed by the formula

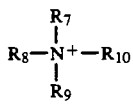

(where $R^7$, $R^8$, $R^9$ represent the same or different alkyl groups having a carbon number of 8-18, and $R_{10}$ represents hydrogen or an alkyl group having a carbon number of 1-8, and a triphenyl tin chloride expressed by the formula

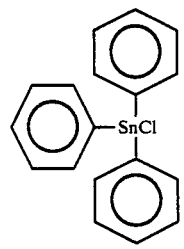

(v) For calcium ion

Suitable examples are bis[di-(octylphenyl) phosphate], (-)-(R,R)-N,N'-bis[11-ethoxy carbonyl) undecyl]-N,N',4,5-tetramethyl-3,6-dioxaoctane-diamide and calcium bis[di(n-decyl) phosphate].

(vi) For hydrogencarbonate ion

Examples which can be mentioned are a quaternary ammonium salts expressed by the formula

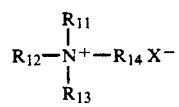

(where $R_{11}$, $R_{12}$, $R_{13}$ represent the same or different alkyl groups having a carbon number of 8-18, $R_{14}$ represents hydrogen atom or an alkyl group having a carbon number of 1 -4, and $X^-$ represents $Cl^-$, $Br^-$ or $OH^-$), tertiary amine compounds expressed by the formula

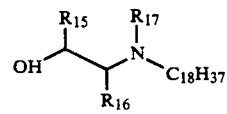

(where $R_{15}$ represents a phenyl group, hydrogen atom or a methyl group, $R_{16}$ represents hydrogen atom or a methyl group, and $R_{17}$ represents a methyl group or an octadecyl group), and a compound expressed by the formula

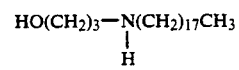

-continued

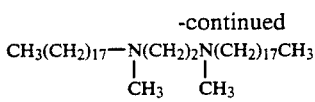

Examples of the electrolytic salt are sodium tetrakis(p-chlorophenyl) borate, potassium tetrakis(p-chlorophenyl) borate, and a compound expressed by the formula

where $R_{18}$ represents an alkyl group, preferably an alkyl group having a carbon number of 2-6.

Examples of the polymer compound are organic polymer compounds such as vinyl chloride resin, vinyl chloride ethylene copolymer, polyester, polyacryl amide and polyurethane, and inorganic polymer compounds such as silicone resin Compounds are used in which the plasticizer does not readily elute Examples of such a plasticizer are dioctyl sebacate ester, dioctyl adipate ester, dioctyl maleate ester and di-n-octyl phenylphosphonate.

To deposit an ion-selective layer on the surface of the redox layer, a preferred process is to prepare a solution by dissolving 50-500 parts by weight of a plasticizer, 0.1-50 parts by weight of an ion carrier substance and an electrolyte salt in 100 parts by weight of a polymeric compound serving as a carrier, dip the substrate electrode (the electrode coated with the redox layer) into the solution, lift the electrode from the solution and blow-dry it for 3 min at a temperature of 80° C. The dipping, lifting and drying steps are repeated 30 times. It is preferred that the ion carrier have a film thickness of 50 μm-3 mm, particularly 0.3-2 mm. An alternative method of obtaining an ion carrier film is to mix a vinyl chloride paste, an ion carrier substance, a plasticizer and an electrolyte salt in the proportions mentioned above, place the mixture on the substrate electrode to a thickness of 50μm-3 mm, and apply heating at a temperature of 150° C. for 1 min to form a gel, thus providing the ion carrier film If the ion-selective film thus deposited has a film thickness of, say, 1 mm, its resistance will be $10^3$-$10^6 \Omega/cm^2$. This makes it possible to effectively prevent the influence of dissolved oxygen in the solution under examination, as well as the influence of other coexisting substances.

Figure 1:
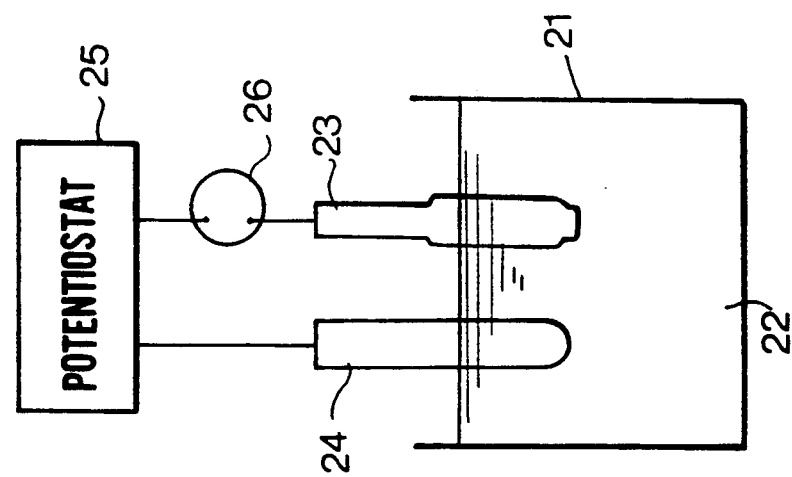
FIG. 1 is a diagrammatic view illustrating an example of an apparatus used in the method of the present invention.

FIG. 1 shows an example of a set-up for measuring the ionic concentration of the solution of interest using the above-described electrochemical ion sensor. The solution, shown at numeral 22, is poured into a tank 21. Numeral 23 denotes the electrochemical ion sensor, and 24 designates a reference electrode, such as a silver/silver chloride electrode or calomel electrode. The ion sensor 23 and reference electrode 24 are immersed in the solution 22. Electrolysis is carried out while holding the potential of the electrochemical ion sensor 23 constant with respect to the reference electrode 24 by means of a potentiostat 25. A current that flows at this time is measured by an ammeter 26. The ionic concentration of the solution is read from a previously prepared calibration curve in which current is plotted against ionic concentration.

Figure 5:
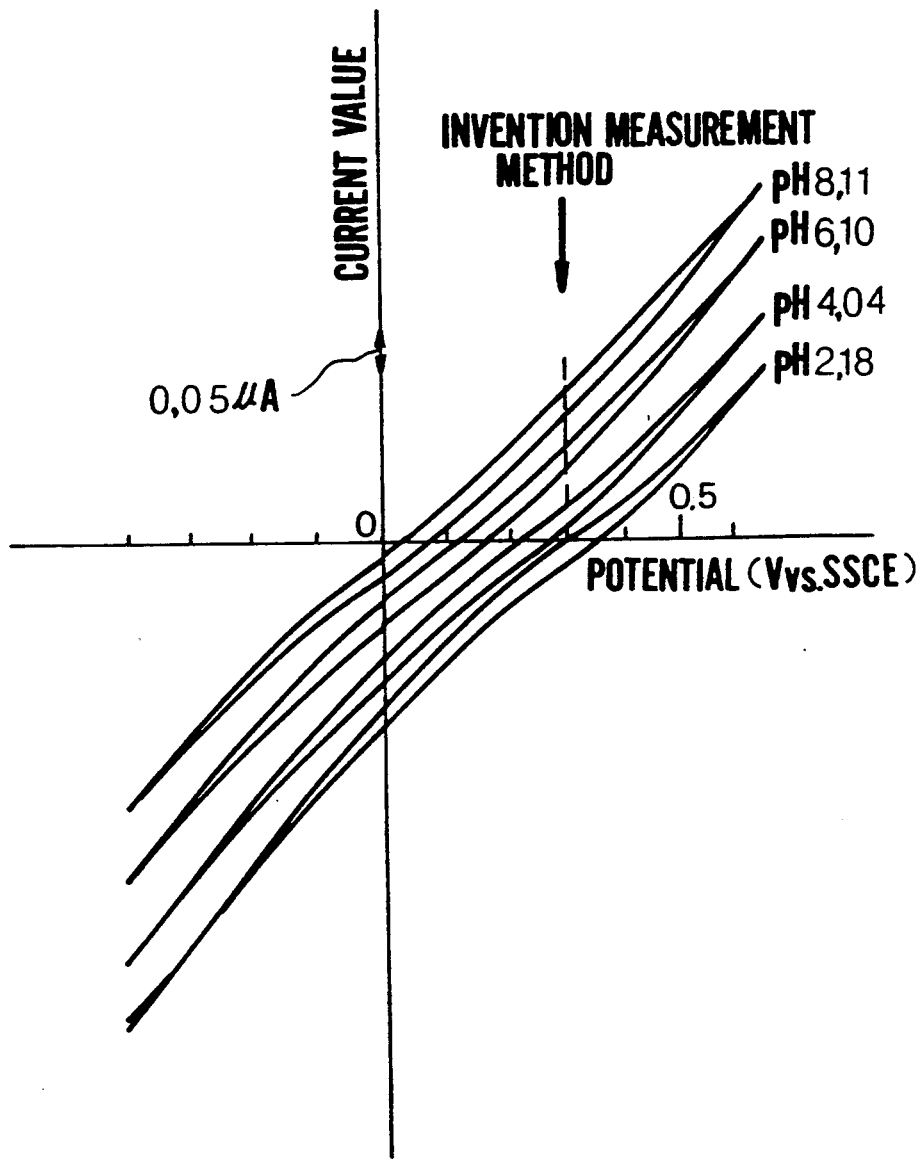
FIG. 5 is a cyclic voltammogram obtained by using a pH sensor as a working electrode.

If a cyclic voltammogram is taken at a sufficiently low sweep rate (e.g. 2 mV/sec) when the electrochemical ion sensor used in the invention and the reference electrode are immersed in a standard solution, current-potential curves of the kind shown in FIG. 5 are obtained. In the waveforms obtained, the magnitude of the current depends essentially upon the electrode film resistance. If electrolysis is carried out under the above conditions while the potential of the electrochemical ion sensor is held constant with respect to the reference electrode in a standard solution having various ionic concentrations, then the observed current will exhibit a substantially linear relationship with respect to the logarithm of ionic concentration.

In accordance with the method of the present invention, the observed current is proportional to the logarithm of the ionic concentration. Therefore, in accordance with the inventive method, ionic concentration can be precisely measured over a wide range just as with the potentiometric method despite the fact that amperometry is employed.

Referential examples and examples illustrating the present invention will now be described.

REFERENTIAL EXAMPLE 1

The pH sensor illustrated in FIG. 2 was fabricated by the following method:

(i) A plate of BPG (manufactured by Union Carbide) was cut into a cylinder 11 having a diameter of 5 mm. A lead wire 16 was connected to the bottom portion 11b by using an electrically conductive adhesive (C-850-6, manufactured by Amicon K.K ). The resulting unit was insulated by insulator 12a with being covered with heat-shrinkable tubing 12b (manufactured by Alpha Wire Company) in such a manner that the upper end face 11a of the BPG cylinder 11 projects slightly from the tubing. The projecting tip of the BPG substrate thus fabricated was then peeled away with a knife blade to expose a new underlying surface Next, electrolytic oxidation was carried out under the following conditions using the above electrode as a working electrode, using a saturated sodium chloride calomel electrode (SSCE) as a reference electrode, and adopting a platinum mesh as a counter electrode:

Electrolytic solution

The electrolytic solution used was acetonitrile containing 0.2 M of sodium perchlorate as a supporting electrolyte and 0.5 M of 2,6-xylenol.

Electrolytic conditions:

An electrolyzing potential was swept three times (sweep rate: 50 mV/sec) from 0 to 1.5 V, followed by carrying out constant-potential electrolysis for 10 min at 1.5 V.

An electrolytic oxidative polymeric film (thickness about 30 μm) 13 of 2,6-xylenol was thus formed on the exposed end face of the BPG substrate. The electrolytic oxidative polymeric film was dark blue in color.

(ii) After being washed with water and then dried, the electrolytic oxidative polymeric film-coated electrode fabricated in (i) above was dipped in a solution of a hydrogen ion carrier having a composition described hereinbelow. The electrode was then removed from the solution and dried. As a result, a hydrogen-ion selective film 14 was deposited on the electrolytic oxidative polymeric film 13. These dipping and drying steps were repeated 20 times so that the hydrogen-ion selective film 14 formed had a thickness of about 0.24 mm. To determine the electrode resistance, the sensor, a variable voltage source and a standard resistor (100 MΩ) were connected in series and the relationship between current and voltage prevailing in such a set-up was investigated using an electrometer. The electrode resistance was calculated from this relationship. The resistance was found to be $8\times 10^4 \Omega/cm^2$ based on measurement made at 37° C. using a phosphate buffer solution having a pH of 7.4. The resistance of an electrode coated only with a polymeric film of 2,6-xylenol was less than $1\times 10^3\Omega/cm^2$. It was thus found that the electrode resistance of the pH sensor fabricated by the above method depends on the resistance of the ion-selective film.

| Dipping solution composition: | |
| --- | --- |
| tri-n-dodecyl amine | 40.2 mg |
| tetrakis p-chlorophenyl potassium borate | 24.4 mg |
| polyvinyl chloride (mean degree of polymerization: 1050) | 1312.6 mg |
| di(2-ethyl hexyl) sebacate | 2622.6 mg |
| tetrahydrofuran | 10 ml |

EXAMPLE 1

Figure 3:
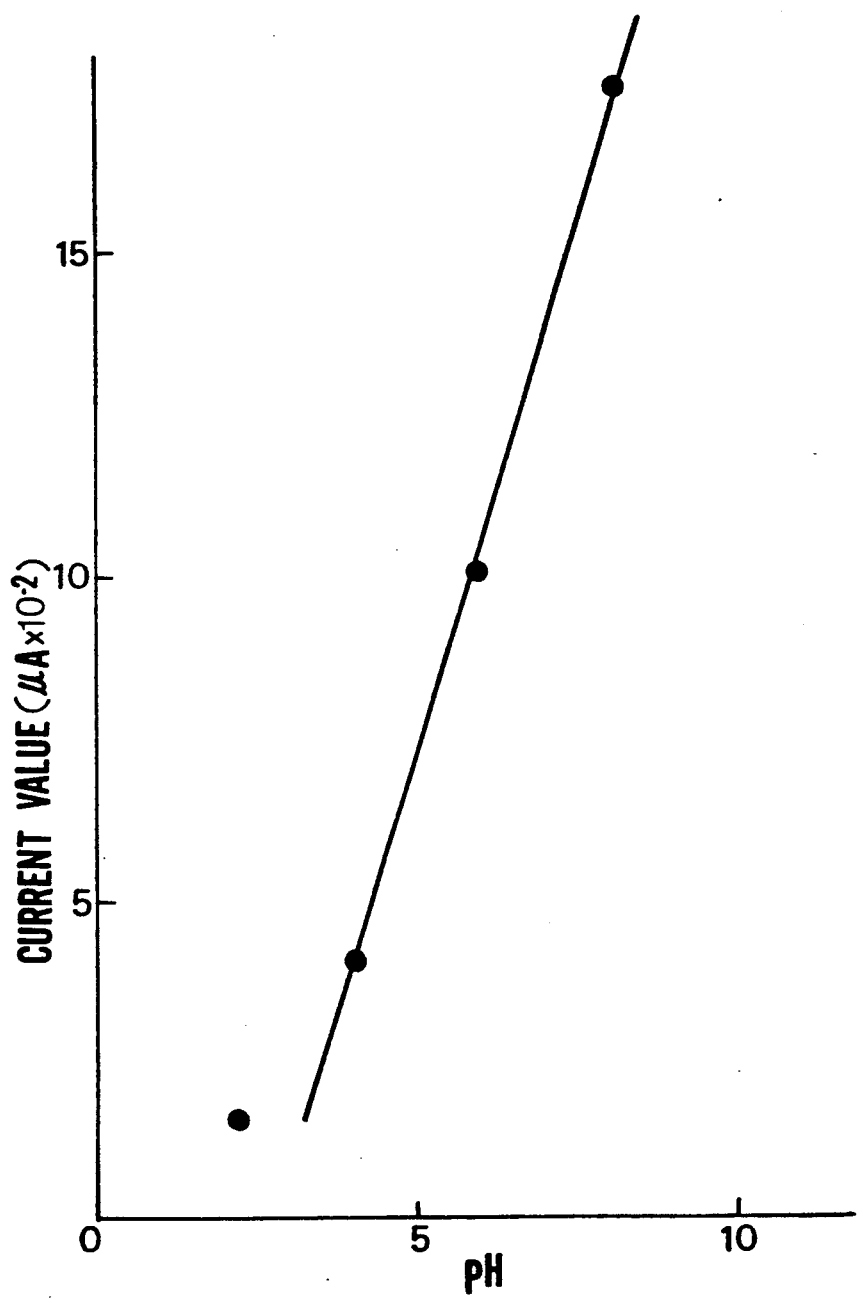
FIGS. 3 and 4 are graphical representations showing the relationship between pH and electric current.

The pH sensor obtained in Referential Example 1 and a SSCE were immersed in standard phosphate buffer solutions (pH 2,18, 4.04, 6.01, 8.11) and the potential of the pH sensor with respect to the SSCE was regulated to 0.3 V. The steady-state value of current was measured about 5 sec after the application of voltage The results are shown in FIG. 3, from which it is clear that the values of pH and current are linearly related within a range of pH 4–8, indicating that pH can be measured amperometrically.

REFERENTIAL EXAMPLE 2

A pH sensor was fabricated as in Referential Example 1, with the exception of the fact that the load of tetrahydrofuran in the dipping solution mentioned in (ii) was changed to 20 ml and the film thickness of the hydrogen ion-selective film was made 0.48 mm. Upon measuring the electrode resistance as in Referential Example 1, the resistance value was found to be $1.5\times 10^5\Omega/cm^2$.

EXAMPLE 2

Figure 4:
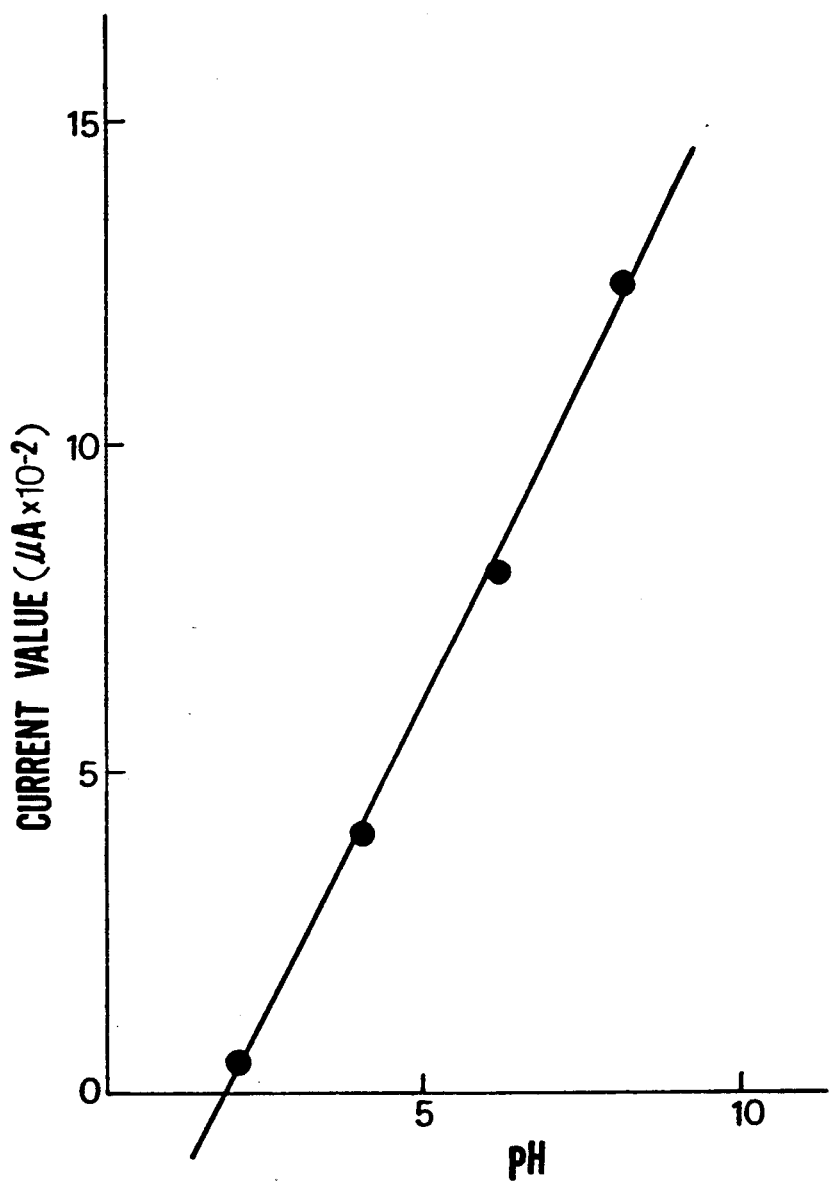

Using the pH sensor obtained in Referential Example 2, current was measured as in Example 1. The results are shown in FIG. 4, from which it is clear that the values of pH and current are linearly related within a range of pH 2 –8. FIG. 5 shows the cyclic voltammogram obtained through measurement with a cell of the same construction.

REFERENTIAL EXAMPLE 3

A pH sensor was fabricated as in Referential Example 1, with the exception of the fact that 1-aminopyrene was used instead of 2,6-xylenol as a monomer of the electrolytically oxidized polymeric film. The electrode resistance, measured as in Referential Example 1, was found to be $8\times 10^4\Omega/cm^2$.

EXAMPLE 3

Figure 6:
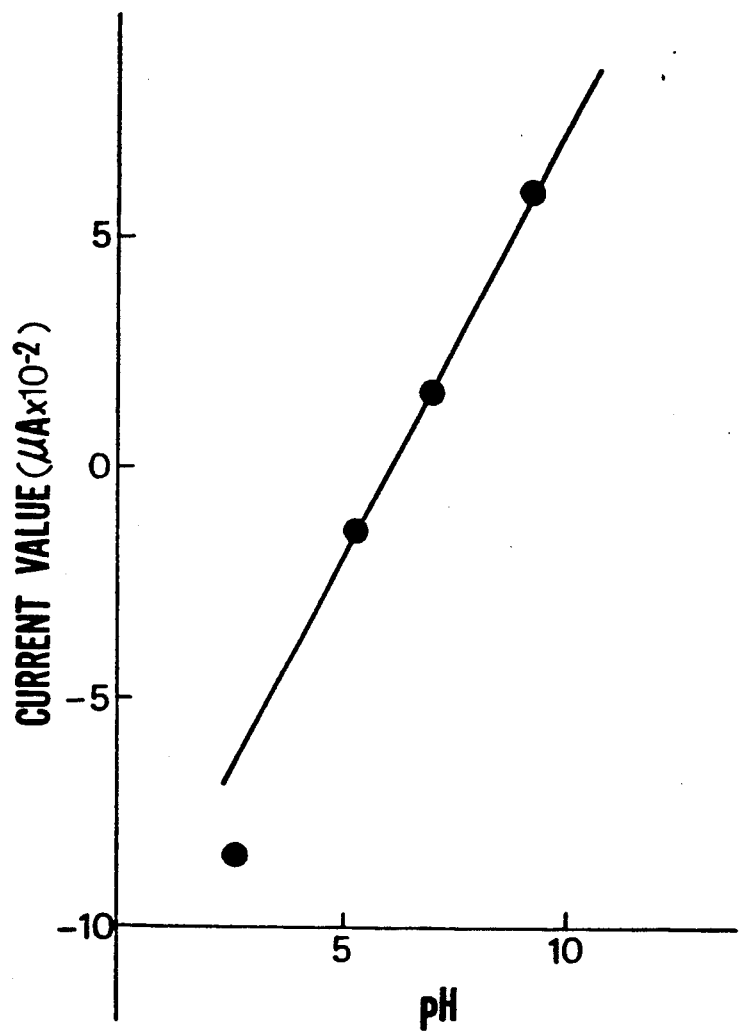
FIG. 6 is a graphical representation showing the relationship between pH and electric current.

Using the pH sensor obtained in Referential Example 3, current was measured as in Example 1. The results are shown in FIG. 6, which shows that the values of pH and current are linearly related within a range of pH 2-8.

REFERENTIAL EXAMPLE 4

An electrolytic oxidative polymeric film-coated electrode was fabricated as in (i) of Referential Example 1. The electrode was then dipped in a solution containing a sodium ion carrier having a composition set forth hereinbelow. The electrode was then removed from the solution and dried. As a result, a sodium-ion selective film was deposited on the electrolytic oxidative polymeric film. These dipping and drying steps were repeated 30 times so that the sodium-ion selective film formed had a thickness of about 0.3 mm. The electrode resistance, measured as in Referential Example 1, was found to be $1\times 10^5\Omega/cm^2$.

EXAMPLE 4

Figure 7:
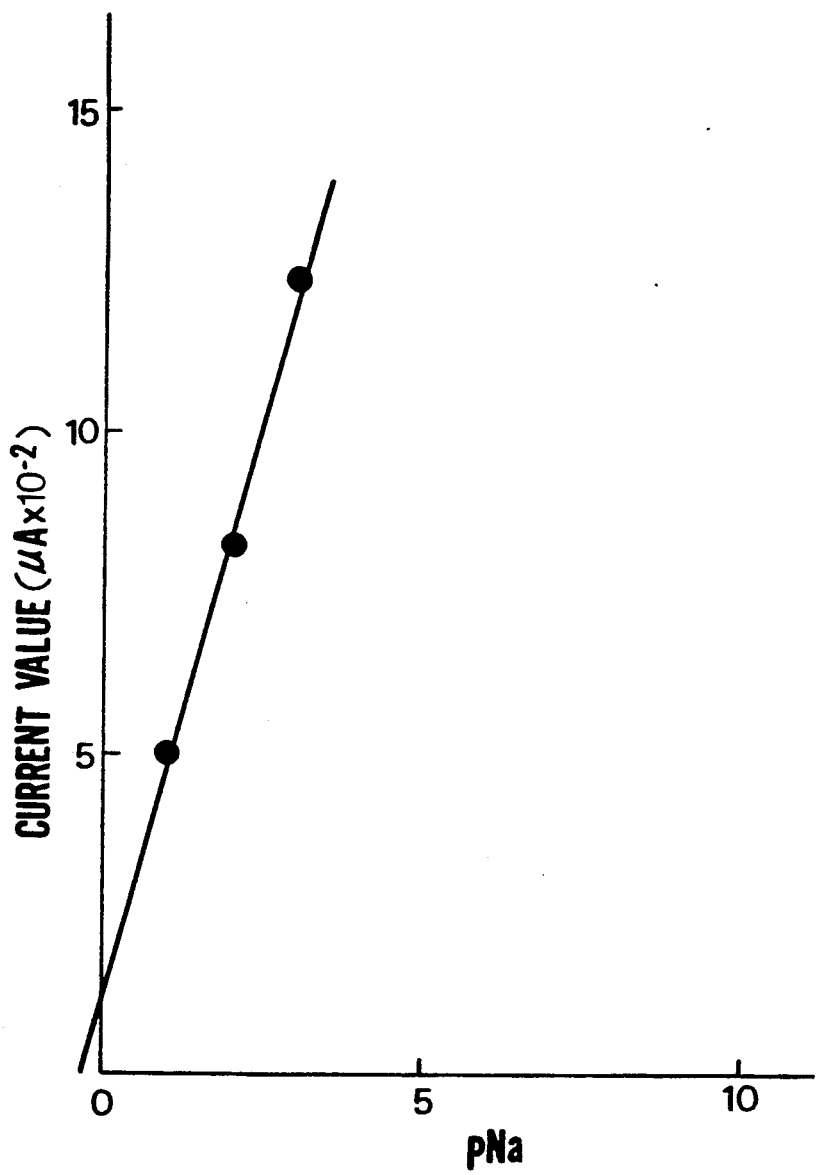
FIG. 7 is a graphical representation showing the relationship between pNa and electric current.

The sodium ion sensor obtained in Referential Example 4 and a SSCE were immersed in $10^{-1}$–$10^{-3}$M sodium chloride solutions and the potential of the sodium ion sensor with respect to the SSCE was regulated to 0.6 V. The steady-state value of current was measured about 10 sec after the application of voltage. The results are shown in FIG. 7, from which it is clear that the values of pNa and current are linearly related within a range of pNa 1–3, indicating that pNa can be measured amperometrically.

As many apparently widely different embodiments of the present invention can be made without departing from the spirit and scope thereof, it is to be understood that the invention is not limited to the specific embodiments thereof except as defined in the appended claims.

What is claimed is:

1. A method of measuring ionic concentration comprising the steps of:
    forming an electrochemical cell by immersing an electrochemical ion sensor having a resistivity of more than $10^3\Omega/cm^2$ and a reference electrode into a solution of interest;
    measuring a current which flows through said electrochemical cell while the electrochemical ion sensor is held at a constant potential with respect to the reference electrode; and
    determining ionic concentration value from the measured current on the basis of proportional relation between the measured current and the logarithm of the ionic concentration;
    said electrochemical ion sensor comprising an electrically conductive substrate, an electrolytically polymerized redox polymer layer fixing a material capable of undergoing a quinone-hydroquinone type redox reaction coating a surface of said electrically conductive substrate, and an ion selective layer exhibiting ion selectivity which is carried on a polymeric compound coating a surface of said redox polymer layer.

2. A method of measuring ionic concentration comprising the steps of:
    forming an electrochemical cell by immersing an electrochemical ion sensor having a resistivity of more than $10^3\Omega/cm^2$ and a reference electrode into a solution of interest;
    measuring a current which flows through said electrochemical cell while the electrochemical ion sensor is held at a constant potential with respect to the reference electrode; and
    determining ionic concentration value from the measured current on the basis of the proportional relation between the measured current and the logarithm of the ionic concentration;
    said electrochemical ion sensor comprising an electrically conductive substrate, an electrolytically polymerized redox polymer layer fixing a material capable of undergoing an amine-quinoid type redox reaction coating a surface of said electrically conductive substrate, and an ion selective layer exhibiting ion selectivity which is carried on a polymeric compound coating a surface of said redox polymer layer.

3. A method of measuring ionic concentration comprising the steps of:

forming an electrochemical cell by immersing an electrochemical ion sensor having a resistivity of more than $10^3 \Omega/cm^2$ and a reference electrode into a solution of interest;

measuring a current which flows through said electrochemical cell while the electrochemical ion sensor is held at a constant potential with respect to the reference electrode; and determining ionic concentration value from the measured current on the basis of proportional relation between the measured current and the logarithm of the ionic concentration;

said electrochemical ion sensor comprising an electrically conductive substrate, an electrolytically polymerized redox polymer layer fixing a member selected from the group consisting of poly(pyrrole) and poly(thionylene) coating a surface of said electrically conductive substrate, and an ion selective layer exhibiting ion selectivity which is carried on a polymeric compound coating a surface of said redox polymer layer.

* * * * *